United States Patent
Gleeson et al.

(10) Patent No.: US 9,066,848 B2
(45) Date of Patent: Jun. 30, 2015

(54) PROCESS FOR MAKING STERILE ARIPIPRAZOLE OF DESIRED MEAN PARTICLE SIZE

(71) Applicant: Bristol-Myers Squibb Company, Tokyo (JP)

(72) Inventors: Margaret M. Gleeson, Berkeley Heights, NJ (US); Soojin Kim, Demarest, NJ (US); Donald C. Kientzler, Hightstown, NJ (US); San Kiang, Madison, NJ (US)

(73) Assignee: Otsuka Pharmaceuticals Co., Ltd., Tokyo (JP)

( * ) Notice: Subject to any disclaimer, the term of this patent is extended or adjusted under 35 U.S.C. 154(b) by 0 days.

(21) Appl. No.: 13/771,691

(22) Filed: Feb. 20, 2013

(65) Prior Publication Data

US 2013/0161848 A1 Jun. 27, 2013

Related U.S. Application Data

(63) Continuation of application No. 13/046,138, filed on Mar. 11, 2011, now abandoned, which is a continuation of application No. 10/968,481, filed on Oct. 19, 2004.

(60) Provisional application No. 60/513,886, filed on Oct. 23, 2003.

(51) Int. Cl.
*A61J 3/02* (2006.01)
*C07D 215/227* (2006.01)
*B01D 9/00* (2006.01)
*B01J 2/06* (2006.01)

(52) U.S. Cl.
CPC .................. *A61J 3/02* (2013.01); *B01D 9/0009* (2013.01); *B01D 9/0054* (2013.01); *B01D 9/0081* (2013.01); *B01J 2/06* (2013.01); *C07D 215/227* (2013.01)

(58) Field of Classification Search
CPC ............ A61J 3/02; A61K 9/0019; A61K 9/10; A61K 9/14; A61K 31/496; B01D 9/0009; B01D 9/0054; B01D 9/0081; B01D 9/02; B01D 9/005; B01D 9/0063; B01D 2009/0086; B01J 2/06; C07D 215/227
USPC .................. 264/12, 11; 424/489; 514/253.08, 514/253.07, 58; 117/65; 422/245.1; 23/295.1, 300, 295 R, 299; 536/46; 423/659; 137/896; 239/421, 433; 366/173; 544/363
See application file for complete search history.

(56) References Cited

U.S. PATENT DOCUMENTS

| | | | |
|---|---|---|---|
| 5,006,528 | A | 4/1991 | Oshiro et al. |
| 5,314,506 | A | 5/1994 | Midler et al. |
| 6,267,989 | B1 | 7/2001 | Liversidge et al. |
| 6,302,958 | B1 | 10/2001 | Lindrud et al. |
| 6,558,435 | B2 | 5/2003 | Am Ende et al. |
| 7,491,726 | B2 | 2/2009 | Parthasaradhi et al. |
| 2004/0005256 | A1 | 1/2004 | Wei et al. |
| 2004/0005257 | A1 | 1/2004 | Wei et al. |
| 2004/0058935 | A1 | 3/2004 | Bando et al. |
| 2005/0032811 | A1 | 2/2005 | Brown |

OTHER PUBLICATIONS

Mahajan et al, "Micromixing effects in a two-impinging-jets precipitator," American Institute of Chemical Engineers, 1996, 42(7), pp. 1801-1814.

*Primary Examiner* — John Pak
*Assistant Examiner* — Nathan W Schlientz
(74) *Attorney, Agent, or Firm* — Finnegan, Henderson, Farabow, Garrett & Dunner, LLP

(57) ABSTRACT

A process is provided for making sterile aripiprazole having an average particle size less than 100 microns but preferably greater than 25 microns employing an impinging jet crystallization procedure. The resulting bulk aripiprazole of desired particle size may be used to form a sterile freeze-dried aripiprazole formulation, which upon constitution with water and intramuscular injection releases aripiprazole over a period of at least about one week and up to about eight weeks.

15 Claims, 1 Drawing Sheet

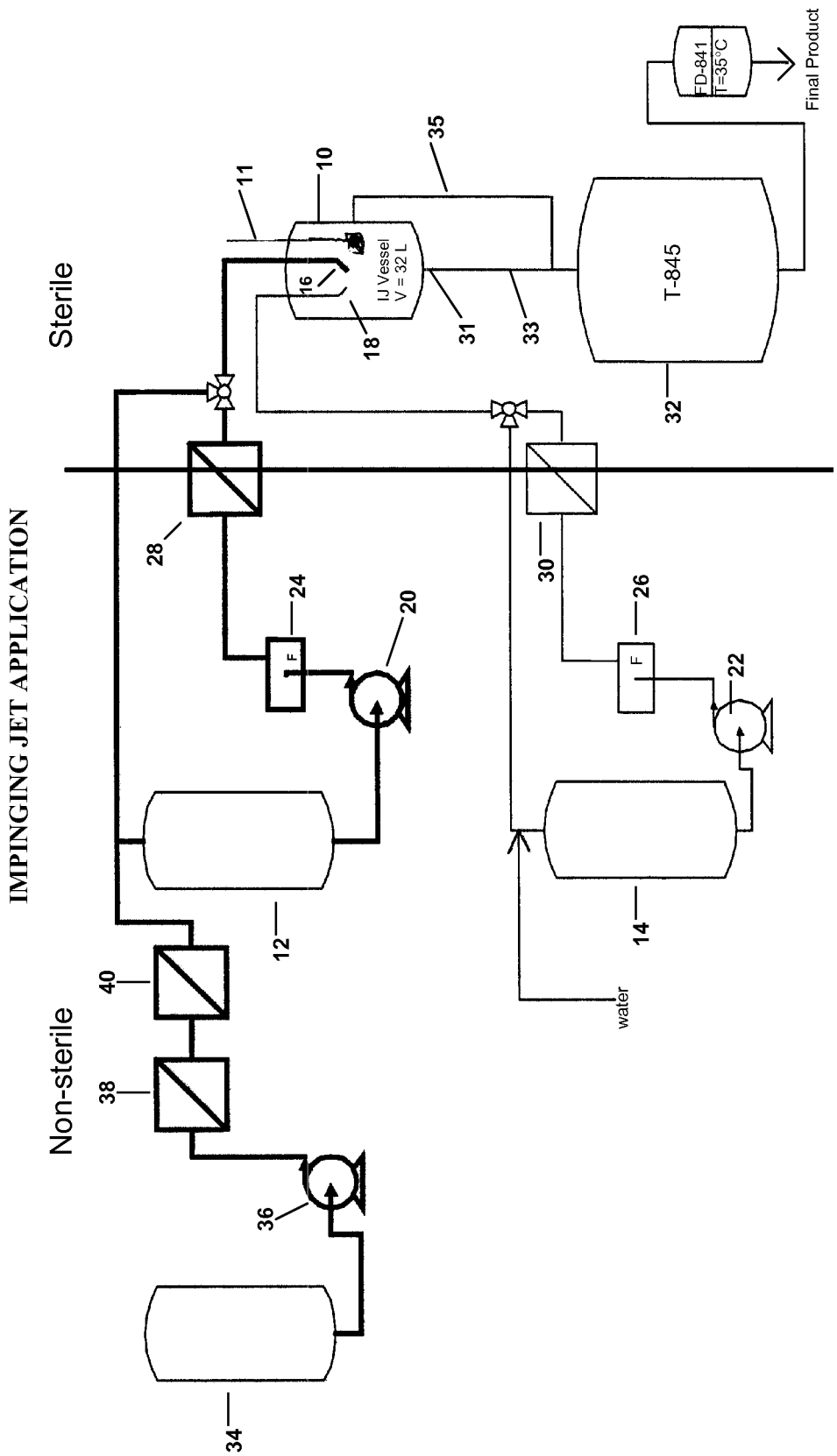

PROCESS FOR MAKING STERILE ARIPIPRAZOLE OF DESIRED MEAN PARTICLE SIZE

CROSS REFERENCE TO RELATED APPLICATION

This Continuation application claims the benefit of U.S. Ser. No. 13/046,138 filed Mar. 11, 2011, now abandoned, which claims the benefit of application U.S. Ser. No. 10/968,481 filed Oct. 19, 2004, now abandoned, which claims the benefit of U.S. Provisional Application Ser. No. 60/513,886, the entire disclosure of which is herein incorporated by reference.

FIELD OF THE INVENTION

The present invention related to a process for making sterile aripiprazole of desired particle size distribution and mean particle size which is especially adapted for use in preparing a controlled release formulation which releases aripiprazole over at least one week or more.

BACKGROUND OF THE INVENTION

U.S. provisional application No. 60/513,618, discloses a controlled release sterile injectable aripiprazole formulation in the form of a sterile suspension, and a method for preparing a sterile freeze-dried aripiprazole formulation (employed in forming the injectable formulation) which includes the steps of:

(a) preparing sterile bulk aripiprazole preferably having a desired particle size distribution and mean particle size within the range from about 5 to about 100 microns, more preferably from about 10 to about 90 microns, (b) preparing a sterile vehicle for the sterile bulk aripiprazole, (c) combining the sterile bulk aripiprazole and the sterile vehicle to form a sterile primary suspension, (d) reducing the mean particle size of aripiprazole in the sterile primary suspension to within the range from about 0.05 to about 30 microns, to form a final sterile suspension, and (e) freeze drying the final sterile suspension to form a sterile freeze-dried suspension of the aripiprazole of desired polymorphic form (anhydrous, monohydrate, or a mixture of both).

In carrying out the above method for preparing the freeze-dried aripiprazole formulation, it is required that everything be sterile so that sterile aripiprazole and sterile vehicle are combined aseptically to form a sterile suspension and that the sterile suspension be freeze-dried in a manner to form sterile freeze-dried powder or cake. Thus, an aseptic procedure is employed to produce sterile bulk aripiprazole of desired mean particle size, and particle size distribution, by crystallization methods as opposed to ball milling. The sterile bulk aripiprazole preferably prepared in step (a) by means of the impinging jet crystallization method, has a desired small particle size and narrow particle size distribution, high surface area, high chemical purity, and high stability due to improved crystal structure.

The impinging jet crystallization utilizes two jet streams that strike each other head-on. One of the streams carries a solution rich in the aripiprazole and the other carries an anti-solvent, such as water. The two streams strike each other which allows for rapid homogeneous mixing and supersaturation due to high turbulence and high intensity of micromixing upon impact. This immediate achievement of supersaturation initiates rapid nucleation. In general, the average crystal size of the aripiprazole decreases with increasing supersaturation and decreasing temperature of the anti-solvent. Therefore, in order to obtain the smallest particle size, it is advantageous to have the highest possible concentration of the aripiprazole rich solution and the lowest temperature of the anti-solvent.

The technique employed for forming sterile bulk aripiprazole is important since particle size of the aripiprazole formulation controls its release profile in the blood system over a period of one month.

It has been found that batch crystallization of aripiprazole produces particles 100 microns. However, in formulating the controlled release sterile aripiprazole injectable formulation discussed above, the particle size of the aripiprazole needs to be 95%≤100 microns. In addition, a narrow particle size distribution is needed to maintain control of the release profile. Milling of batch aripiprazole is undesirable, as a broad particle size distribution will be obtained. Thus, it would be advantageous to employ a technique for preparing sterile bulk aripiprazole which can reduce particle size of aripiprazole to 95%≤100 microns with a narrower particle size distribution than attainable employing batch crystallization.

U.S. Pat. No. 5,006,528 to Oshiro et al. discloses 7-[(4-phenylpiperazino)-butoxy]carbostyrils, which include aripiprazole, as dopaminergic neurotransmitter antagonists.

Aripiprazole which has the structure

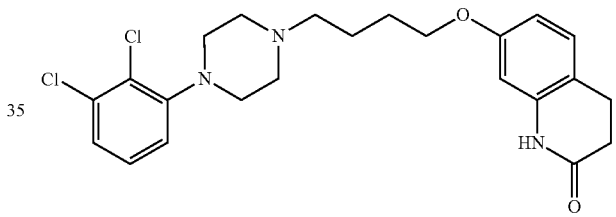

is an atypical antipsychotic agent useful in treating schizophrenia. It has poor aqueous solubility (<1 μg/mL at room temperature).

U.S. Pat. No. 6,267,989 to Liversidge, et al. discloses a method for preventing crystal growth and particle aggregation in nanoparticulate compositions wherein a nanoparticulate composition is reduced to an optimal effective average particle size employing aqueous milling techniques including ball milling.

U.S. Pat. No. 5,314,506 to Midler, et al. discloses a process for the direct crystallization of a pharmaceutical having high surface area particles of high purity and stability wherein impinging jet streams are employed to achieve high intensity micromixing of particles of the pharmaceutical followed by nucleation and direct production of small crystals.

U.S. Pat. No. 6,302,958 to Lindrud et al. discloses a method and apparatus for crystallizing submicron-sized crystals of a pharmaceutical composition employing sonication to provide ultrasonic energy in the immediate vicinity of impinging fluid drug and solvent streams so as to effect nucleation and the direct production of small crystals.

U.S. application Ser. No. 10/419,418, filed Apr. 21, 2003 by Chenkou Wei which is based on U.S. Provisional Applications Nos. 60/376,414, filed Apr. 29, 2002 and 60/439,066, filed Jan. 9, 2003 entitled "Crystallization System Using Atomization" discloses a method for crystallizing a pharmaceutical by atomizing one solution and introducing the atomized solution into a vessel containing a second solution where the solutions are mixed to form a product, which does not require post-crystallization milling. This application is incorporated herein by reference.

U.S. application Ser. No. 10/419,647, filed Apr. 21, 2003 by Chenkou Wei which is based on U.S. Provisional Applications Nos. 60/379,351, filed May 10, 2002 and 60/439,057, filed Jan. 9, 2003 entitled "Crystallization System Using Homogenization" discloses a process for crystallizing a chemical material from a first solution and a second solution wherein the first solution is atomized and introduced into a second solution, and the atomized solution and second solution are mixed to form the product. This application is incorporated herein by reference.

BRIEF DESCRIPTION OF THE INVENTION

In accordance with the present invention, there is provided a process for preparing sterile bulk aripiprazole of desired small particle size and narrow particle size distribution, preferably having an average particle size less than about 100 microns but preferably greater than 25 microns, which includes the steps of:

(a) providing a jet stream of a solution of aripiprazole in an organic solvent, preferably ethanol, preferably heated at a desired elevated temperature;

(b) providing a jet stream of anti-solvent, preferably water, which is capable of initiating precipitation of aripiprazole from solution, preferably said anti-solvent being at a desired temperature below the temperature of the solution of aripiprazole;

(c) causing the jet stream of solution of aripiprazole in solvent and the jet stream of anti-solvent to strike each other and impinge on one another to create high turbulence at their point of impact, each jet stream having sufficient linear velocity to achieve high intensity micromixing of each stream prior to nucleation, to produce a slurry of crystals of aripiprazole monohydrate; and (d) recovering crystals of aripiprazole monohydrate of desired small particle size and narrow particle size distribution.

Prior to step (d) ultasonic energy may be provided, by means of a sonication probe, as described in U.S. Pat. No. 6,302,958, the disclosure of which is incorporated herein by reference, the tip of which is positioned within a gap defined between the two jet streams, to cause the impinging jet streams to achieve high intensity micromixing of fluids prior to nucleation.

In addition, in accordance with the present invention, a preferred process is provided for preparing sterile bulk aripiprazole of desired average particle size of less than about 100 microns, but preferably greater than 25 microns, and narrow particle size distribution, which includes the steps of:

(a) providing a jet stream of a solution of aripiprazole in ethanol heated at a temperature within the range from about 70 to about 85° C., preferably from about 75 to about 80° C.;

(b) providing a jet stream of deionized water which is at a temperature within the range from about 2 to about 40° C., preferably from about 20 to about 35° C.;

(c) causing the jet streams of solution of aripiprazole and water, each at a flow rate (where jet nozzles of 0.02 inch internal diameter are employed) within the range from about 0.20 to about 0.30 kg/min, preferably from about 0.22 to about 0.28 kg/min, to impinge on one another to create high turbulence at their point of impact to achieve high intensity micromixing of each stream prior to nucleation, and form a slurry of crystals of aripiprazole monohydrate; and (d) recovering crystals of aripiprazole monohydrate having an average particle size less than 100 microns, but preferably greater than 25 microns, preferably about 95% of the crystals having a particle size less than 100 microns.

Prior to step (d) ultasonic energy may be provided, by means of a sonication probe, as described above, the tip of which is positioned within a gap defined between the two jet streams, to cause the impinging jet streams to achieve high intensity micromixing of fluids prior to nucleation.

In carrying out the above process of the invention, the volumetric ratio of solution of aripiprazole in organic solvent to anti-solvent is within the range from about 0.5:1 to about 1.5:1, preferably from about 0.9:1 to about 1.1:1.

The above processes may also be employed to prepare crystals of aripiprazole monohydrate having an average particle size of less than 25 microns.

The processes of the invention as described above employs jet streams which impinge on each other to achieve high intensity micromixing of the streams to enable formation of a homogeneous composition prior to the start of nucleation in a continuous crystallization process. Nucleation and precipitation are initiated utilizing the effect of antisolvent addition on the solubility of the aripiprazole in the solvent therefore.

The sonication steps disclosed above are carried out as described in U.S. Pat. No. 6,302,958.

The aripiprazole produced by the process of the invention may be employed in forming sterile bulk aripiprazole having a desired particle size distribution, preferably 10%<10 microns, 50%<35 microns and 95%<100 microns, and mean particle size within the range from about 25 to about 100 microns.

The sterile bulk aripiprazole prepared by the process of the invention may be used in forming a sterile-freeze dried aripiprazole formulation which may be suspended in water to form an injectable aripiprazole formulation as described in U.S. provisional application Ser. No. 10/419,647.

Each of the above embodiments of the process of the invention are referred to as the impinging jet crystallization process of the invention.

The process of the invention employs impinging jet crystallization technology, an example of which is disclosed in U.S. Pat. No. 5,314,506 to Midler et al.

It will also be appreciated that the sterile bulk aripiprazole of desired small particle size and narrow particle size distribution as described above may be prepared employing the process and apparatus described and claimed in each of the Chendou Wei applications entitled "Crystallization System Using Atomization" and "Crystallization System Using Homogenization" described above and incorporated herein by reference.

BRIEF DESCRIPTION OF THE DRAWINGS

The accompanying FIGURE is a schematic representation of an impinging jet crystallization process flow diagram used in carrying out the process of the invention, which includes a crystallizer vessel.

DETAILED DESCRIPTION OF THE INVENTION

The process of the invention is illustrated in the following reaction scheme:

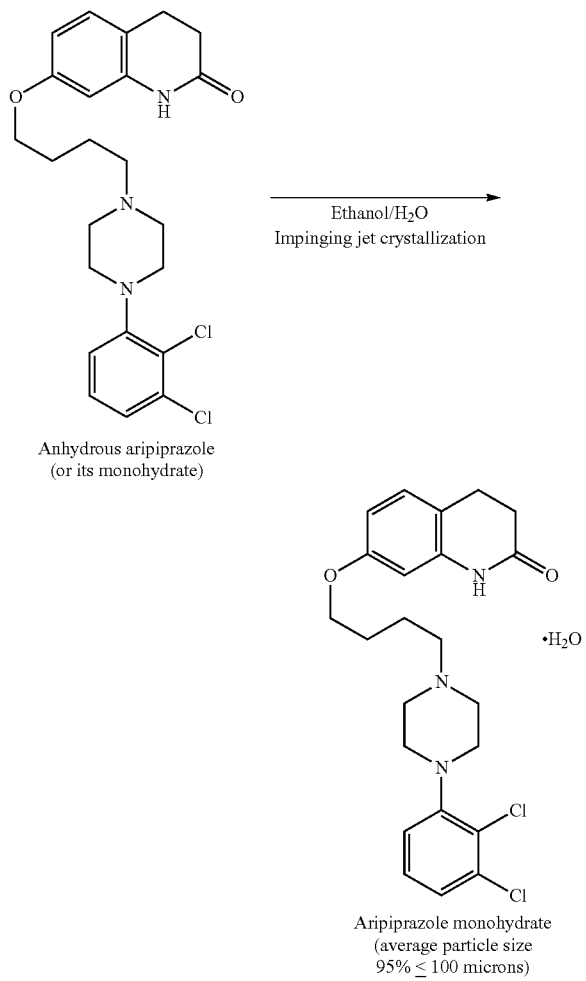

In carrying out the process of the invention, low pyrogen aripiprazole starting material is employed to ensure that the sterile aripiprazole of desired particle size will be produced. The low pyrogen aripiprazole starting material may be either the anhydrous form or the monohydrate form. Either material will yield the desired monohydrate form from the impinging jet crystallization process of the invention.

The process of the invention employs two jet nozzles to create two impinging jet streams to achieve high intensity micromixing of the streams prior to nucleation and formation of crystals of aripiprazole monohydrate. The two impinging jet streams should be substantially diametrically opposed to one another with the nozzles directed to face each other. The jet nozzles will be aligned and positioned so that the fluid streams will impact head-on and will impinge. When the jet nozzles are properly aligned and appropriate flow rates chosen, the two streams will form a plane when impinged.

Each of the process streams, namely the aripiprazole-organic solvent stream and the anti-solvent stream will be sterilized. To sterilize the two process streams, both streams are preferably polish filtered and then sterile filtered through an appropriate size filter, such as a 0.2 micron filter. The aripiprazole stream should be filtered at an elevated temperature, for example, about 80° C., to prevent precipitation.

The temperature and composition of each solution are chosen so that 1) no material will crystallize upstream of the impinging jets, and 2) sufficient supersaturation will be developed in the impinging jets to cause nucleation. Micromixing creates temperature and compositional uniformity throughout the mixture prior to the start of nucleation.

To obtain the smallest particle size of aripiprazole, the highest possible concentration of aripiprazole in the organic solvent should be employed. Thus, the starting solution of aripiprazole in organic solvent, preferably ethanol, will contain from about 0.01 to about 0.1 kg/L aripiprazole, preferably from about 0.04 to about 0.06 kg/L aripiprazole. In a most preferred embodiment, the aripiprazole will be present in an amount of about 0.05 kg/L.

The organic solvent will preferably be ethanol, most preferably from about 92 to about 97% ethanol, with the remainder being water.

Other organic solvents, such as methanol, ethyl acetate, acetone, acetonitrile, acetic acid or isopropyl alcohol or mixtures of two or more thereof, or mixtures with water may be employed.

The anti-solvent will preferably be deionized water.

The two streams, namely, the stream of the solution of aripiprazole in the organic solvent and the stream of anti-solvent, are characterized as jet streams in that they will be made to strike each other head on at high linear velocities with a minimum of 5 m/s. The flow rates will be determined by the diameter of the jet nozzles employed to deliver the streams and the rate at which the streams are pumped through the nozzles. In a preferred embodiment, the flow rate of each of the stream of aripiprazole/solvent and the stream of antisolvent will be essentially the same, but will of course be in opposite directions.

The flow rates will be chosen so that proper impinging is achieved. For example, where jet nozzles of 0.02 inch internal diameter are employed, flow rates will be within the range from about 0.20 to about 0.30 kg/min, preferably from about 0.22 kg/min to about 0.28 kg/min, more preferably from about 0.24 kg/min to about 0.26 kg/min, and optimally about 0.25 kg/min.

The temperature of each of the streams is important in determining ultimate size of the particles of aripiprazole produced. Thus, the aripiprazole-solvent (preferably ethanol) stream should be heated at a temperature within the range from about 70 to about 85° C., preferably from about 75 to about 80° C. The anti-solvent stream (preferably water) should be at a temperature substantially less than the temperature of the aripiprazole-solvent stream, and within the range from about 2 to about 40° C., preferably from about 20 to about 35° C., and optimally about 30° C.

The two streams strike each other head-on, from opposite directions, to cause rapid homogeneous mixing and supersaturation due to high turbulence and high intensity of mixing upon impact. The immediate achievement of supersaturation initiates rapid nucleation. In general, the average crystal size decreases with increasing supersaturation and decreasing temperature of the anti-solvent. The smallest particle size of aripiprazole is obtained employing the highest possible concentration of the aripiprazole solution and the lowest temperature of the anti-solvent. Sonication is utilized where even smaller particles are desired.

DESCRIPTION OF THE FIGURE

Referring to the accompanying FIGURE, an impinging jet crystallization process flow diagram and crystallizer vessel used in carrying out the process of the invention are shown which includes a jacketed impingement crystallization vessel 10. There are two jacketed-vessels 12, 14 that flank the impingement vessel 10 to the left and right which contain the aripiprazole-rich solution (12) and the anti-solvent (14), respectively. Both of these side vessels 12, 14 are spaced apart from the impingement vessel 10. Impinging jet nozzles 16, 18, each having a 0.02-inch diameter, are spaced 10 mm apart. The impingement vessel 10 may include agitator 11 and a sonicator (as employed in U.S. Pat. No. 6,302,958), if desired, not shown for drawing clarity. Outlet 31 of impingement vessel 10 is connected to receiving vessel 32, via line 33. Overflow line 35 links impingement vessel 10 and line 33 and aids in maintaining a constant volume in impingement vessel 10.

The above description is of the sterile portion of the flow diagram. The non-sterile portion as shown includes a vessel 34 for holding a solution of aripiprazole in ethanol, preferably 95% ethanol, which is pumped via pump 36 through polish filter 38 and sterile filter 40 into vessel 12 and processed as described above.

The jet nozzles 16, 18 should be placed so that the fluid streams they emit will impinge, inside the stirred impingement vessel 10 or inside a separate jet chamber (not shown) which is linked directly to the vessel 10. The fluid jets must impinge to create an immediate high turbulence impact. The two jet nozzles are preferably arranged so that they are substantially diametrically opposed to each other with their outlet tips directed to face each other; i.e., the two jet nozzles are at or close to a 180 degree angle to each other from an overhead view. Preferably, each jet outlet nozzle can have a slight downward angle from the horizontal, for example, about 10 degrees, to help the flowing material move down and out of the chamber.

Likewise, two jet nozzles placed directly inside the stirred impingement vessel 10 are preferably arranged so that they are substantially diametrically opposed to each other with their outlet tips directed to face each other. When the jet nozzles are so placed, each nozzle can have a slight upward or downward angle from the horizontal of from 0 degrees up to about 15 degrees, but preferably the two nozzles have just enough downward angle from the horizontal (ca. 13 degrees) to ensure that the fluid stream of one will not enter the outlet hole of the opposite nozzle.

Jet nozzle 16 is used to transport aripiprazole solution into the vessel 10 (or separate jet chamber) and the other jet 18 is used to similarly transport water. The distance between the nozzle tips inside the jet chamber or vessel 10 should be such that the hydro-dynamic form of each fluid jet stream remains essentially intact up to the point of impingement. Therefore, the maximum distance between the nozzle tips will vary depending on the linear velocity of the fluids inside the jet nozzles. To obtain good results for generally non-viscous fluids, linear velocity in the jet nozzles should be at least about 5 meters/sec., more preferably above 10 meters/sec., and most preferably between about 20 to 25 meters/sec., although the upper limit of linear velocity is only limited by the practical difficulties involved in achieving it. Linear velocity and flow rate can both be controlled by various known methods, such as altering the diameter of the entry tube and/or that of the nozzle outlet tip, and/or varying the strength of the external force that moves the fluid into and through the nozzle. Each jet apparatus can be manipulated independently to attain a desired final fluid composition ratio. When the desired flow ratio of one jet to the other differs from unity, preferably the difference is compensated for by appropriate sizing of the entry tubes. For example, if a 4:1 volumetric ratio of feed solution to anti-solvent is desired, the entry tube delivering feed solution should be twice the diameter of the entry tube delivering anti-solvent. When the jet streams impinge inside a jet chamber, residence time for the fluid inside the jet chamber is typically very short, i.e., less than ten seconds.

Stirring in the vessel is provided by standard agitators 11, preferably Rushton 10 turbines, Intermig impellers, or other agitators suitable for stirring a slurry suspension. Any impeller providing good circulation inside the vessel may be used. However, when the jet streams are arranged to impinge directly inside the stirred vessel, an agitator that does not interfere with the space occupied by the impinging jet streams inside the vessel is preferred, especially, e.g., a Rushton turbine. Impinging jet streams inside the vessel are most preferably placed in the effluent stream of the agitator, and the height of the liquid in the stirred vessel 10 when operated in continuous mode (i.e., flow in equals flow out, constant volume maintained), is most preferably between about two to four times the height of the impeller.

The crystallization is preferably run in a continuous process and the appropriate residence time for the completion of crystal digestion is attained by adjusting the volume capacity of the stirred vessel, but the mixture can be held up in the vessel for any desired length of age time if batchwise processing is desired.

Manual seeding can be done at any point in the system, e.g., in the stirred vessel 10, the transfer line or the jet chamber itself. In some situations, the continuous jet process may be "self-seeding", i.e., the first crystals to form inside the jet chamber (if used), the transfer line (if used) or the stirred vessel 10 serve as seed for the material that flows through thereafter.

The micromixed material must be highly supersaturated to attain the beneficial results of the jet crystallization process. Aside from thermoregulated initiation of nucleation, temperature variation also affects product results when anti-solvent is used to initiate nucleation because of its effect on supersaturation. Generally, good results can be achieved using a volumetric ratio of aripiprazole to anti-solvent that provides a high degree of supersaturation in the jet chamber in a temperature range of about 24° C. to 70° C., although the temperature upper limit is limited only by the chosen solvent's boiling point.

An example of the impingement vessel which may be employed is disclosed in U.S. Pat. No. 5,314,506 to Midler et al. and in U.S. Pat. No. 6,302,958 to Lindrud et al. which are incorporated herein by reference.

To prepare a 100-gram batch of aripiprazole monohydrate, a 100 grams of aripiprazole anhydrous N1 is charged into a 4-L vessel 12 and dissolved in 2 L of 95% ethanol at 75 to 80° C. The clear solution is then transferred to the product-rich 2-L jacketed vessel 10 and maintained at 75 to 80° C. In the anti-solvent vessel 14, 2 L of deionized (DI) water is then charged and heated to 28 to 32° C. When both liquids are at the desired temperatures, the two streams are pumped simultaneously via pumps 20 and 22 through mass flow meters 24, 26, respectively, and sterile filters 28, 30, respectively, through the 0.02-inch internal diameter nozzles 16, 18 and impinge at a rate of 0.22 to 0.28 kg/min to produce the monohydrate crystals. The crystals are continuously transferred to receiving vessel 32 to maintain a constant volume in the impingement vessel 10. It takes approximately 5 to 7 minutes to impinge a 100-gram batch. The slurry is cooled to 20 to 25° C., filtered, and washed with 200 mL of deionized water. The cake is then dried at 35° C. under vacuum to obtain approximately 100 grams of aripiprazole monohydrate, H0, with a Karl Fisher % (KF %) of ca. 4% w/w.

EXAMPLES

The following working Examples represent preferred embodiments of the present invention.

Example 1

Sterile bulk active pharmaceutical ingredient (API) aripiprazole was prepared using impinging crystallization with sonication employing an apparatus set up as shown in the attached FIGURE.

The following procedure was employed to form a sterile bulk aripiprazole.

1. Charge 100 g of aripiprazole in a 4 L flask 34.
2. Add 2 L of 95% ethanol.
3. Heat the suspension to 80° C. until it becomes a clear solution.
4. Transfer the hot aripiprazole solution to a 2 L jacketed vessel 12 and maintain at 75-80° C.
5. Charge 2 L of deionized (DI) water to a 2 L jacketed vessel 14.
6. Cool the DI water to 2° C.
7. Add 100 mL of 95% ethanol and 100 mL of DI water to the impinging vessel 10 and cool to 2° C.
8. Initiate sonication (Sonication is provided by a 0.5 inch probe with 120 W power output employed as described in U.S. Pat. No. 6,302,958).
9. Pump the aripiprazole solution through a 0.02 inch diameter nozzle 16 at 0.25 kg/min and impinge it with the 2° C. water pumped at 0.25 kg/min through a 0.02 inch diameter nozzle 18.
10. Sonicate the newly formed crystal slurry in the impinge vessel 10 while continuously transferring the crystals to a receiving vessel 32 to maintain a constant volume in the impingement vessel 10.
11. Cool the slurry to 20 to 25° C. at the end of impingement.
12. Filter the slurry.
13. Wash the cake with 200 mL of DI water.
14. Dry the wet cake at 35° C. under vacuum to obtain 97.9 g of aripiprazole with a KF of 4.0% w/w, with reduced particle size (95%<100 microns).

Example 2

Sterile bulk API aripiprazole was prepared using impinging jet crystallization and an apparatus set up as shown in the accompanying FIGURE.

The following procedure was employed to form a sterile bulk aripiprazole:

1. Suspend 100 g of aripiprazole in 2000 mL of 95% ethanol. Heat the suspension to 80° C. until it becomes a clear solution.
2. Polish filter the aripiprazole solution into a holding vessel 12 and maintain at 80° C.
3. Polish filter 2000 mL water to another holding vessel 14 and heat to 80° C.
4. Pump the aripiprazole solution through a 0.02 inch diameter nozzle 16 at 0.25 kg/min and impinge it with the 30° C. water pumped at 0.25 kg/min through a 0.02 inch diameter nozzle 18 to form a crystal slurry which is collected in an impingement vessel 10.
5. Agitate the newly formed crystal slurry in the impingement vessel 10 while continuously transferring it to a receiver 32 to maintain a constant volume in the impingement vessel 10.
6. At the end of impingement, cool the slurry in the receiver 32 to room temperature.
7. Filter the slurry.
8. Dry the wet cake at 35° C. under vacuum to yielding 100 g (96% recovery) of aripiprazole with reduced particle size (95%<100 microns).

Example 3

An aripiprazole injectable aqueous suspension (200 mg aripiprazole/2 mL, 200 mg/vial) was prepared as follows.

The following ingredients were added to a 3 L glass jacketed vessel maintained at 15° C. (±5° C.) to form a sterile primary suspension:

| | |
|---|---|
| Aripiprazole (prepared by impinging jet crystallization as described in Example 2): | 100 g |
| Carboxymethylcellulose, Sodium Salt 7L2P | 9.0 g |
| Mannitol | 45 g |
| Sodium Phosphate, Monobasic | 0.8 g |
| Sodium Hydroxide Solution, 1N | q.s. to adjust pH to 7.0 |
| Water, USP | q.s. to 1000 g |

The sterile suspension was mixed at 500-1000 rpm for about 0.5 hour and then at 300-500 rpm for an additional 1 hour under 20" Hg (±5"Hg) vacuum.

2.5 mL of the above suspension were aseptically filled into sterilized vials which were then aseptically partially stoppered with sterilized stoppers. The vials were aseptically transferred to a freeze dryer and lyophilized according to the following cycle:

(a) thermal treatment: freeze product at −40° C. over 0.1-1 h and keep at −40° C. for at least 6 h, (b) cool the condenser to −50° C. or below, (c) primary drying: lower chamber pressure to approximately 100 microns Hg and increase product temperature to −5° C. over approximately 2 h; continue primary drying at −5° C. and 100 microns Hg for at least 48 h, (d) stopper the vials under atmospheric pressure or partial vacuum using sterile nitrogen or air and remove from the freeze dryer, (e) seal the vials with the appropriate seals and label.

What is claimed is:

1. A process for preparing sterile crystals of aripiprazole monohydrate of desired small particle size and narrow particle size distribution without milling, which comprises:

a) providing a jet stream of a solution of aripiprazole in an organic solvent, wherein the jet stream of the solution of aripiprazole in an organic solvent is heated to a temperature within the range from 70 to 85° C.;

b) providing a jet stream of anti-solvent at a temperature within the range from 2 to 40° C. which is capable of initiating precipitation of aripiprazole from solution, wherein each of said aripiprazole-organic solvent stream and said anti-solvent stream is sterilized;

c) causing the jet stream of aripiprazole in the organic solvent and the jet stream of anti-solvent to strike each other at a flow rate of each which is the same or different but is within the range from 0.2 to 0.3 kg/min where jet nozzles of 0.02 inch internal diameter are employed and impinge on one another to create high turbulence at their point of impact to achieve high intensity micromixing of each stream prior to nucleation, to produce a slurry of crystals of aripiprazole monohydrate, and d) recovering crystals of aripiprazole monohydrate, wherein 10% of the crystals of aripiprazole monohydrate have a particle size of less than 10 microns, 50% of the crystals of aripiprazole monohydrate have a particle size of less than 35 microns, and 95% of the crystals of aripiprazole monohydrate have a particle size of less than 100 microns, and the mean particle size of the crystals of aripiprazole monohydrate are within the range of from 25 microns to 100 microns.

2. The process as defined in claim 1 further including the step of providing ultrasonic energy in the immediate vicinity of said impinging jet streams, so as to effect nucleation and the direct production of small crystals of aripiprazole monohydrate.

3. The process as defined in claim 1 wherein the organic solvent for the aripiprazole is ethanol, methanol, ethyl acetate, acetone, acetonitrile, acetic acid or isopropyl alcohol, or mixtures of one or more thereof, or mixtures with water.

4. The process as defined in claim 1 wherein the organic solvent for the aripiprazole is ethanol or a mixture of ethanol and water.

5. The process as defined in claim 1 wherein the anti-solvent is water.

6. The process as defined in claim 1 wherein the volumetric ratio of solution of aripiprazole in organic solvent to anti-solvent is within the range from about 0.5:1 to about 1.5:1.

7. The process as defined in claim 1 wherein the aripiprazole-solvent stream and the anti-solvent stream are in about a 1:1 volume ratio.

8. The process as defined in claim 1 wherein the organic solvent comprises ethanol.

9. A process for preparing sterile crystals of aripiprazole monohydrate of desired small particle size and narrow particle size distribution without milling, which comprises:
   a) providing a jet stream of a solution of aripiprazole in ethanol/water heated at a temperature within the range from 70 to 85° C., wherein said stream is also sterilized;
   b) providing a jet stream of deionized water which is at a temperature within the range from about 2 to about 40° C., wherein said stream is also sterilized;
   c) causing the jet stream of the solution of aripiprazole in ethanol and the jet stream of water each at a flow rate within the range from about 0.2 to 0.3 kg/min, where jet nozzles of 0.02 inch internal diameter are employed, to impinge on one another to create high turbulence at their point of impact to achieve high intensity micromixing of each stream prior to nucleation, to form a slurry of crystals of aripiprazole monohydrate; and
   (d) recovering crystals of aripiprazole monohydrate, wherein 10% of the crystals of aripiprazole monohydrate have a particle size of less than 10 microns, 50% of the crystals of aripiprazole monohydrate have a particle size of less than 35 microns, and 95% of the crystals of aripiprazole monohydrate have a particle size of less than 100 microns, and the mean particle size of the crystals of aripiprazole monohydrate are within the range of from 25 microns to 100 microns.

10. The process as defined in claim 9 further including the step of providing ultrasonic energy in the immediate vicinity of said impinging jet streams, so as to effect nucleation and the direct production of small crystals of aripiprazole monohydrate.

11. The process as defined in claim 9 wherein the aripiprazole has a low pyrogen content.

12. The process as defined in claim 9 wherein the aripiprazole-ethanol/water solution contains from about 0.10 to about 0.1 kg/L aripiprazole.

13. The process as defined in claim 9 wherein the stream of aripiprazole in ethanol/water and the stream of deionized water flow in opposite directions and form a plane when they impinge one another, and strike each other to cause rapid homogeneous mixing and supersaturation due to high turbulence and high intensity of micromixing upon impact, which initiates rapid nucleation.

14. The process as defined in claim 9 wherein average crystal size decreases with increasing concentration of aripiprazole in ethanol and supersaturation and decreasing temperature of the deionized water.

15. The process as defined in claim 9 wherein the aripiprazole-ethanol/water stream and the deionized water stream are in about a 1:1 volume ratio with each other.

* * * * *